United States Patent [19]
Rohrbach et al.

[11] 4,292,199
[45] Sep. 29, 1981

[54] METHOD OF PREPARING A SUPPORT MATRIX

[75] Inventors: Ronald P. Rohrbach, Forest Lake; Mary J. Maliarik, Lake Forest, both of Ill.

[73] Assignee: UOP Inc., Des Plaines, Ill.

[21] Appl. No.: 178,659

[22] Filed: Aug. 18, 1980

[51] Int. Cl.³ .................... B01J 31/06; C12N 11/08
[52] U.S. Cl. .................... 252/430; 252/428; 435/180
[58] Field of Search ................ 252/430, 428; 435/180

[56] References Cited
U.S. PATENT DOCUMENTS 4,141,857  2/1979  Levy et al. .................... 252/430

Primary Examiner—Patrick Garvin
Attorney, Agent, or Firm—James R. Hoatson, Jr.; Eugene I. Snyder; William H. Page, II

[57] ABSTRACT

An improved method of preparing support matrices, characterized as inorganic oxides impregnated with a polyamine cross-linked with a bifunctional reagent so as to furnish a plurality of pendant functional groups, comprises impregnating the oxide at a pH less than about 4 and subsequently curing the polyamine-impregnated oxide at a pH from about 8 to about 12. This improved method leads to subsequently prepared immobilized enzyme systems whose activity is increased by about 35%.

9 Claims, No Drawings

METHOD OF PREPARING A SUPPORT MATRIX

BACKGROUND OF THE INVENTION

Enzyme-catalyzed reactions have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes are water soluble, and if they are merely used in aqueous solutions recovery of enzymes for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in U.S. Pat. No. 4,141,857, where a polyamine is absorbed on a mwetal oxide such as alumina, treated with an excess of a bifunctional reagent, such as glutaraldehyde, so as to cross-link the amine, and then contacting the mass with enzyme to form covalent bonds between the pendant aldehyde groups and an amino group on the enzyme. The support matrix prepared according to the aforementioned invention has great utility in immobilizing reactive chemical entities, enzymes being but one class of such reactive chemical entities.

Since enzymes which are to be immobilized on, or bound to, such a support matrix are relatively expensive, it is highly desirable to maximize utilization of the enzyme. One manifestation of increased utilization is increased activity of the resulting immobilized enzyme system. By immobilized enzyme is meant the support matrix bearing the immobilized or bound enzyme. It has been found that deposition of a polyamine onto a porous, refractory inorganic oxide under highly acidic conditions followed by increasing the pH to a relatively basic state affords a support matrix capable of significantly increased loading of the enzyme upon itssubsequent immobilization, thereby affording an immobilized enzyme system of significantly greater activity.

SUMMARY OF THE INVENTION

An object of this invention is to increase the loading of an enzyme onto a support matrix which may be characterized as a porous, refractory inorganic oxide impregnated with a polyamine which is subsequently cross-linked with an excess of a bifunctional reagent so as to furnish a plurality of pendant functional groups. An embodiment comprises impregnating the oxide with a polyamine at a highly acidic pH, and subsequently curing the impregnated oxide at a basic pH prior to contacting with a bifunctional reagent. In a more specific embodiment, the polyamine is polyethyleneimine initially deposited at a pH less than about 4 and subsequently cured at a pH from about 8 to about 12.

DESCRIPTION OF THE INVENTION

The support matrix as described in U.S. Pat. No. 4,141,857 has found broad utility. It may be described as a porous, refractory inorganic oxide impregnated with a polyamine which is subsequently cross-linked with an excess of a bifunctional reagent so as to furnish a plurality of pendant functional groups. A discovery leading to this invention is that the activity of a subsequently prepared immobilized enzyme system depends on the pH at which the polyamine is impregnated and on the pH of a later curing period. This effect is most pronounced when the oxide is in the form of larger particles, that is pellets or granules greater than about 1/32 of an inch in size, with the effect becoming more pronounced the larger the particles.

The support matrices to which this invention applies are comprised of porous, refractory inorganic oxides, such as alumina, thoria, magnesia, silica and combinations thereof, glass, or ceramics bearing or impregnated with a polyamine reacted with an excess of a bifunctional reagent so as to cross-link the polyamine and furnish a plurality of functional groups pendant to the formed polymer. Among the suitable polyamines are included materials such as polyethyleneimine, tetraethylenepentamine, ethylenediamine, diethylenetriamine, triethylenetetramine, pentaethylenehexamine, hexamethylenediamine, and phenylenediamine, with polyethyleneimine being an especially preferred polyamine. Among the bifunctional reagents used are glutaraldehyde, succinidialdehyde, terephthaldehyde, and toluenediisocyanate, glutaraldehyde often being the bifunctional reagent of choice.

the support matrices are prepared as follows. For example, an inorganic oxide, such as gamma alumina, may be contacted with an aqueous solution of a polyamine, such as polyethyleneimine, where the polyamine is present at a concentration from about 1% to about b 50%. Excess liquid is removed by suitable means, as by decantation. The oxide may be washed with water to remove excess polyamine, but it is preferred to merely dry the material by evaporation of the water. An aqueous solution of cross-linking agent, such as glutaraldehyde, containing from about 1% to about 25% of the bifunctional reagent is added in an amount sufficient to provide an excess of from about 3 to about 50 or more moles of said bifunctional reagent per mole of polyamine. This solution is contacted, with occasional mixing, with the polyamine-coated oxide for a time sufficient to ensure equilibrium, generally from about 5 minutes to about 5 hours. Liquid is then removed from the oxide support by suitable means, such as by decantation, and the solid support is washed well with water to remove adhering, but not chemically bound, bifunctional reagent.

The improvement of this invention comprises impregnating a porous, refractory inorganic oxide with a polyamine at a highly acidic pH and curing the impregnated oxide at a basic pH. According to this improvement, impregnation is performed at a pH less than about 4, preferably in the pH range of about 1 to about 3. The time of impregnation is at least 10 minutes, with times of about 60 minutes generally used. The impregnated oxide is then cured at a basic pH. By curing is meant that the polyamine-impregnated oxide is permitted to remain for a time, at least 10 minutes, in a bsic environment of pH from about 8 to about 12, with the preferred pH range being from about 9 to about 11. After the curing period, excess polyamine may be removed by a water wash of the impregnated oxide. In a preferred embodiment, the polyamine-impregnated oxide is merely dried by evaporation of water.

The adjustment of pH during the impregnation and curing steps generally is made by the addition of strong acids and strong bases. Examples of strong acids include hydrochloric acid, sulfuric acid, phosphoric acid, trichloroacetic acid, and so on. The most convenient strong bases to use are the hydroxides of the alkali metals, such as sodium hydroxide, potassium hydroxide, lithium hydroxide, cesium hydroxide, and rubidium hydroxide. However, it is to be emphasized that the choice of strong base or strong acid is not critical so long as the acid or base used does not chemically alter the polyamine or remain on the impregnated oxide in a condition where its subsequent removal is difficult.

The improvement in the method of preparing a support matrix taught herein may be applied to any immobilized reactive chemical entity in which the reactive molecule can react with the pendant functional group without substantial loss of chemical activity. Enzymes form an important class of such reactive molecules, examples of which include glucose isomerase, glucoamylase, lactase, cellulase, glucose oxidase, peroxidase, ribonuclease, urease, histidase, trypsin, papain, hexokinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, deoxyribonuclease, etc. It is to be understood that these enzymes are cited solely for illustrative purposes and it is not to be construed as a limitation of this invention. Other enzymes may be utilized, but not necessarily with equivalent results. Preparation of the immobilized enzyme system generally comprises contacting a solution of the enzyme at a temperature from about 0° C. to about 70° C. for a time from about 4 to about 40 hours, separating excess enzyme solution, as by decantation, and washing the resulting immobilized enzyme system so as to remove adhering but unbound enzyme.

The following examples are for illustrative purposes only, and it is to be understood that this invention is not to be limited thereto.

EXAMPLE 1

In this example, a series of support matrices were prepared at various pH from 1 to 12 under controlled conditions so as to afford valid comparisons of the activity of subsequently prepared immobilized enzyme systems.

To 10 ml of a 2.5% weight-weight solution of polyethyleneimine was added 1.5 ml of gamma alumina as 1/16-inch pellets. The pH of the solution was adjusted to the desired point either with hydrochloric acid or sodium hydroxide, and periodically readjusted if necessary. The mass was stirred one hour under vacuum, after which time the polyamine-impregnated oxide was removed by filtration and air dried to a constant ABD. This dried material was added to 10 ml of a 5% weight-weight solution of glutaraldehyde and mixed occasionally for about one hour, liquid was removed, and the solid was washed well with distilled water until the washings gave a negative fuchsin test. A dried sample of each support matrix so prepared was analyzed for carbon and nitrogen, the results appearing in the Table.

Immobilized glucose isomerase systems were prepared from this series of support matrices by contacting an aqueous solution containing about 3,000 units per gram of enzyme with the support matrix at 4° C. for 40 hours with occasional mixing. Liquid was removed by decantation and the solid was washed well with deionized water to remove adhering but unbound enzyme. The immobilized glucose isomerase systems so prepared were tested in a plug flow reactor using as a feedstock a solution of 45% by weight glucose containing $5 \times 10^{-5}$ magnesium ion and 0.1% sodium sulfite at a pH of 8.0. Initial activities of the systems so prepared are tabulated below.

| POLYMER LOADING AND ENZYME ACTIVITY | | | |
|---|---|---|---|
| pH | %C | %N | activity, units per gram |
| 1 | 1.1 | 0.15 | 330 |
| 4 | 2.8 | 0.64 | 370 |
| 7 | 3.1 | 0.56 | 410 |
| 10 | 4.7 | 0.86 | 360 |
| 12 | 3.8 | 0.53 | 320 |

The table demonstrates at least two important results. Elemental analyses clearly show the amount of cross-linked polyamine in the support matrix changes with pH, varying by about 400%, with a maximum about pH 10. However, the activity of the immobilized enzyme system shows only a small change, with the maximum, if any, occurring at a pH about 7. A conclusion to be drawn from these data is that increased enzymatic activity does not arise merely because of increased amounts of cross-linked polyamine in the support matrix. Another conclusion which may be drawn is that deposition of polamine at various conditions of pH without subsequent curing has little, if any, effect on the activity of the subsequently prepared immobilized enzyme system.

EXAMPLES 2 AND 3

In Example 2, 1/16-inch pellets of alumina were impregnated with polyamine without pH adjustment. In Example 3, alumina in the same form was impregnated with polyethyleneimine at a pH of 1 for about one hour, after which the pH was adjusted to 9 for another hour exposure time. Preparation of the support matrices in these examples was then completed as described in Example 1.

Immobilized glucose isomerase systems were prepared from these two support matrices as described in Example 1 under carefully controlled conditions. The immobilized glucose isomerase prepared from the support matrix of Example 2 had an activity of 250 units per gram; that prepared from Example 3 had an activity of 340 units per gram. Thus, use of the improvement described herein affords an increase in immobilized enzyme activity of greater than 35%. Additionally, the half-life of immobilized glucose isomerase prepared from the support matrix of Example 2 was about 31 days, whereas the half-life of the immobilized enzyme system from Example 3 was about 85 days, thereby showing an improvement of about 174%.

What is claimed is:

1. In a method of preparing a support matrix including impregnating a porous, refractory inorganic oxide with a polyamine, contacting the impregnated oxide with an excess of a bifunctional reagent so as to crosslink the polyamine and furnish a plurality of pendant functional groups, removing unreacted but adhering bifunctional reagent, and recovering the suport matrix, the improvement comprising: impregnating the oxide with a polyamine at a pH less than about 4 and thereafter curing the impregnated oxide at a pH from about 8 to 12.

2. The method of claim 1 wherein the oxide is impregnated with a polyamine at a pH from about 1 to about 3.

3. The method of claim 1 wherein the impregnated oxide is cured at a pH from about 9 to about 11.

4. The method of claim 1 wherein the inorganic oxide is selected from the group consisting of alumina, thoria, magnesia, slica, and combinations thereof.

5. The method of claim 4 wherein the oxide is alumina.

6. The method of claim 1 wherein the polyamine is selected from the group consisting of polyethyleneimine, tetraethylenepentamine, ethylenediamine, diethylenetriamine, triethylenetetramine, pentaethylenehexamine, hexamethylenediamine, and phenylenediamine.

7. The method of claim 6 wherein the polymaine is polyethyleneimine.

8. The method of claim 1 wherein the bifunctional reagent is selected from the group consisting of glutaraldehyde, succindialdehyde, terephthaldehyde, and toluenediisocyanate.

9. The method of claim 1 wherein the bifunctional reagent is glutaraldehyde.

* * * * *